United States Patent

Ono et al.

Patent Number: 5,721,084
Date of Patent: Feb. 24, 1998

[54] CHARGE CONTROLLING AGENT FOR ELECTROSTATIC IMAGE DEVELOPMENT, AND TONER AND CHARGE-IMPARTING MATERIAL EMPLOYING IT

[75] Inventors: Hitoshi Ono; Noriaki Takahashi; Osamu Ando; Masako Takeuchi, all of Kanagawa, Japan

[73] Assignee: Mitsubishi Chemical Corporation, Tokyo, Japan

[21] Appl. No.: 753,914

[22] Filed: Dec. 3, 1996

[30] Foreign Application Priority Data

Dec. 4, 1995 [JP] Japan ................................. 7-315418

[51] Int. Cl.$^6$ .................................................... G03G 9/097
[52] U.S. Cl. ........................................................ 430/110
[58] Field of Search ................................... 430/110, 109

[56] References Cited

U.S. PATENT DOCUMENTS

| 5,385,799 | 1/1995 | Ono et al. ........................... 430/110 |
| 5,389,480 | 2/1995 | Ono et al. . | |

FOREIGN PATENT DOCUMENTS

| 0 503 861 | 9/1992 | European Pat. Off. . |
| 0 548 772 | 6/1993 | European Pat. Off. . |
| 299 034 | 3/1992 | Germany . |

*Primary Examiner*—John Goodrow
*Attorney, Agent, or Firm*—Oblon, Spivak, McClelland, Maier & Neustadt, P.C.

[57] ABSTRACT

A charge controlling agent for electrostatic image development, which is a metallic compound of a compound of the formula (I):

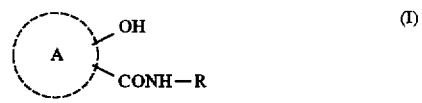

wherein each of A and R is a substituted or unsubstituted aromatic ring residue, and —O and —CONH—R are bonded to positions adjacent to each other on the aromatic ring residue A, or the formula (II):

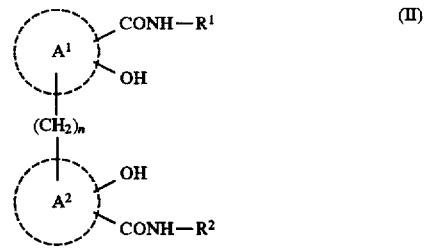

wherein each of $A^1$, $A^2$, $R^1$ and $R^2$ is a substituted or unsubstituted aromatic ring residue, n is an integer, and —O and —CONHR$^1$, and —O and —CONH—R$^2$, are bonded to positions adjacent to each other on the aromatic ring residues $A^1$ and $A^2$, respectively.

13 Claims, No Drawings

CHARGE CONTROLLING AGENT FOR ELECTROSTATIC IMAGE DEVELOPMENT, AND TONER AND CHARGE-IMPARTING MATERIAL EMPLOYING IT

The present invention relates to a charge controlling agent for electrostatic image development to be used for e.g. an electrophotographic copying machine, and a toner and a charge-imparting material to impart an electric charge to a toner useful for development of an electrostatic image, wherein such a charge controlling agent is used.

A developer for e.g. an electrophotographic copying machine is, in a developing process, once deposited on an image-carrier such as a photoreceptor on which an electrostatic image is formed, then in a transfer process, transferred from the photoreceptor to a transfer paper and then in a fixing process, fixed on a copying paper. Here, as the developer for developing the electrostatic image formed on the latent image-maintaining surface, a dual-component developer comprising a carrier and a toner and a mono-component developer (magnetic toner, non-magnetic toner) requiring no carrier, are known.

One of the important properties required for a toner is an electric charge property. A toner is required to have a positive or negative charge of a proper level when contacted with a carrier or with a wall of a developing tank, and the charge level is required to be substantially stable with time even during continuous use or in an adverse environment. An electric charge property may be imparted to the toner by a resin or the colorant itself, but no adequate electric charge property can thereby be imparted. Therefore, it has been known to incorporate to a toner a positive charge-imparting Nigrosine dye or quaternary ammonium salt, or a negative charge-imparting metal-containing monoazo dye, metal salicylate complex or copper phthalocyanine pigment, as an agent (a charge controlling agent) to impart an electric charge property to a toner.

However, these conventional charge controlling agents have some problems with respect to the charge-imparting property or other properties required for a toner. One of the problems is the safety of the toner. Conventional charge controlling agents, particularly negative charge controlling agents, have been mainly of a metal dye type containing a metal such as chromium, since a high charge level can thereby be imparted. However, it is desirable not to use a metal, such as chromium, which is doubtful about the safety, as a component of a material like a toner which is used in the vicinity of human. In recent years, a voice calling for the importance of such safety has been increasingly high. Accordingly, also for the toner, it is desired to develop a charge controlling agent which contains no metal such as chromium and which has a charge-imparting property better than the conventional agents and is excellent also in other properties required for the toner.

A second problem for the toner may be the charge stability. Conventional charge controlling agents are, in many cases, inadequate in the charge stability although their charge level may be high, and thus have a problem such that the charge level changes with time during continuous copying or continuous printing, whereby copy staining tends to result. Such a problem is certainly increasing especially in recent years, since copying machines capable of treating a large number of copies continuously at a high speed, are desired. Accordingly, it is desired to develop a charge controlling agent having a better charge stability.

On the other hand, an attempt to improve the electric charge property of a toner has been conducted not only by means of the above-described charge controlling agent but also by means of a transporting, regulating or friction material such as a carrier, a developing sleeve or a layer-forming blade which is in contact with a toner during the developing process (such a material will hereinafter categorically be referred to as "a charge-imparting material", which generally represents a material or a part capable of imparting an electric charge required for the development to a toner or capable of imparting an electric charge supplementally, in contact with the toner during or prior to the developing process). As such a charge-imparting material, one having high durability against friction with the toner, is required, and as a carrier, one which is useful for a long period of time without replacement, is desired.

Under these circumstances, the present inventors have conducted extensive studies to provide an electrostatic image-developing toner of high quality which is excellent in the charge stability even without containing a hazardous metal such as chromium and which scarcely brings about copy staining and to provide a charge-imparting material which is free from deterioration in the performance during use for a long period of time and which provides an image excellent in gradation and fine line reproducibility. As a result, they have found it possible to solve the above-mentioned problems by employing a certain specific metallic salt of a compound disclosed in JP-A-5-173370 as the charge controlling agent and have arrived at the present invention.

Namely, the object of the present invention is to provide a charge controlling agent which is excellent in the charge stability and which is excellent also in other properties required for a toner, such as moisture resistance, light resistance and heat resistance.

Another object of the present invention is to provide a charge-imparting material and a toner of high quality, whereby the print density is proper and stable even during continuous use or in an adverse environment and copy staining scarcely results.

A still another object of the present invention is to provide a charge controlling agent excellent in the safety.

Accordingly, the present invention provides a charge controlling agent for electrostatic image development, which is a metallic compound of a compound of the formula (I):

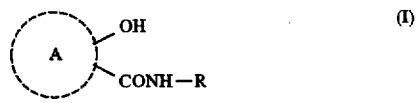

wherein each of A and R is a substituted or unsubstituted aromatic ring residue, and —O and —CONH—R are bonded to positions adjacent to each other on the aromatic ring residue A, or the formula (II):

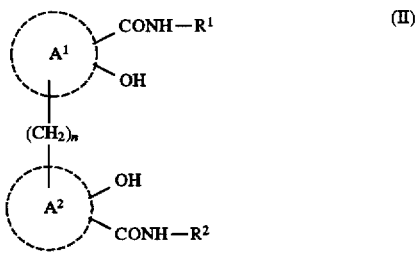

wherein each of $A^1$, $A^2$, $R^1$ and $R^2$ is a substituted or unsubstituted aromatic ring residue, n is an integer, and —O and —CONHR$^1$, and —O and —CONH—R$^2$, are bonded to positions adjacent to each other on the aromatic ring residues $A^1$ and $A^2$, respectively, and a toner and a charge imparting material employing it.

Now, the present invention will be described in detail with reference to the preferred embodiments.

The charge controlling agent for electrostatic image development of the present invention has a feature that it contains at least one metallic compound of a compound of the above formula (I) or (II).

In the formulas (I) and (II), each of A, $A^1$, $A^2$, R, $R^1$ and $R^2$ is an aromatic ring residue, which may have a substituent on its ring, or which may be a hetero ring. Further, it may be a condensed ring having carbon rings, hetero rings, or a carbon ring and a hetero ring, condensed to each other.

Specific examples of such an aromatic ring residue include a benzene ring, a naphthalene ring, an anthracene ring, a phenanthrene ring, a carbazole ring, a fluorene ring, a fluorenone ring, a dibenzofuran ring, a dibenzothiophene ring and a benzocarbazole ring. Preferred are a benzene ring and a naphthalene ring. More preferably, each of A, $A^1$ and $A^2$ is a naphthalene ring, and each of R, $R^1$ and $R^2$ is a benzene ring or a naphthalene ring. Specific examples of the substituents which the aromatic ring residue may have on the ring, include a $C_{1-5}$ alkyl group such as a methyl group, an ethyl group, a propyl group, a n-butyl group or a tert-butyl group; a haloalkyl group such as a trifluoromethyl group; an amino group; an alkoxyl group such as a methoxyl group or an ethoxyl group; a halogen atom such as a chlorine atom or a bromine atom; a nitro group; and a phenyl group. Preferred are a $C_{1-5}$ alkyl group, a haloalkyl group and a halogen atom. More preferred are a chlorine atom and a trifluoromethyl group. The number of substituents is preferably from 1 to 5, and in the case of a plurality of substituents, they may be the same or different from one another. Further, A and R in the formula (I), and $A^1$, $A^2$, $R^1$ and $R^2$ in the formula (II), may be the same or different from one another.

In the formula (II), the alkylene chain connecting $A^1$ and $A^2$ preferably has a carbon number n of from 1 to 5, more preferably from 1 to 3.

The metal used for the metallic compound of a compound of the formula (I) is preferably a bivalent to tetravalent metal. Specific examples include Zn, Ca, Ba, Mg, Al, Fe, Zr and Ti. Preferred are Zn, Ca, Mg and Al. The metal used for the metallic compound of a compound of the formula (II) is preferably a monovalent to tetravalent metal. Specific examples include Na, K, Zn, Ca, Ba, Mg, Al, Fe, Zr and Ti. Preferred are Zn, Ca, Mg and Al.

The metallic compound of a compound of the formula (I) can readily be prepared usually by the following method. Namely, it can be prepared, for example, by boiling and reacting compounds of the following formulas (III) and (IV):

(III)

H$_2$N—R (IV)

wherein A and R are as defined in the formula (I), in a solvent such as toluene or chlorobenzene by an addition of phosphorus trichloride, followed by a salt exchange reaction with a metal.

The metallic compound of a compound of the formula (II) can be obtained by a synthesis as disclosed by Brass, Sommer, Berichte (Bet), 61, 998 (1928), followed by a salt exchange reaction with a metal.

Namely, it can be obtained, for example, by reacting compounds of the formulas (V) and (VI):

(V)

(VI)

wherein $A^1$, $A^2$, $R^1$ and $R^2$ are as defined in the formula (II), in an alkaline solution by an addition of formaldehyde at a temperature of from 50° to 120° C., followed by a salt exchange reaction with a metal.

The metallic compound of a compound of the formula (I) is considered to be a compound of the formula (VII), and the metallic compound of a compound of the formula (II) is considered to be a compound of the formula (VIII):

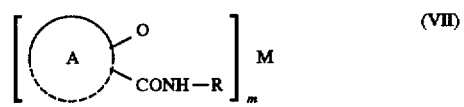

(VII)

wherein A and R are as defined in the formula (I), M is a metal with m valency, m is an integer, and —O and —CONH—R are bonded to positions adjacent to each other on the aromatic ring residue A;

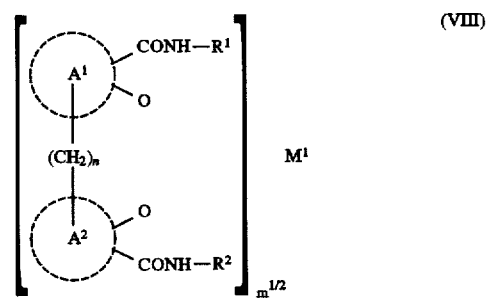

(VIII)

wherein $A^1$, $A^2$, $R^1$, $R^2$ and n are as defined in the formula (II), $M^1$ is a metal with $m^1$ valency, $m^1$ is an integer, and —O and —CONH—$R^1$, and —O and —CONH—$R^2$, are bonded to positions adjacent to each other on aromatic ring residues $A^1$ and $A^2$, respectively.

Among metallic compounds of the compound of the formula (I) or (II), preferred specific examples for charge controlling agent for electrostatic development of the present invention, may be compounds represented by the following structural formulas, but the preferred examples are not limited thereto.

TABLE 1

| No. | A (*1) | R | Valency of metal (m) | Metal (M) | Position of —CONH—R | Position of —O |
|---|---|---|---|---|---|---|
| (1) | Naphthalene | p-Chlorophenyl | 2 | Zn | 2 | 3 |
| (2) | Naphthalene | p-Chlorophenyl | 2 | Ca | 2 | 3 |
| (3) | Naphthalene | p-Chlorophenyl | 3 | Al | 2 | 3 |
| (4) | Naphthalene | p-Chlorophenyl | 4 | Zr | 2 | 3 |
| (5) | 3,5-Dibromobenzene | p-Bromophenyl | 2 | Zn | 1 | 2 |
| (6) | 3,5-Dibromobenzene | p-Bromophenyl | 2 | Ba | 1 | 2 |
| (7) | 3,5-Dibromobenzene | p-Bromophenyl | 3 | Al | 1 | 2 |
| (8) | 3,5-di-tert-butylbenzene | 3,5-di(trifluoro-methyl)phenyl | 2 | Zn | 1 | 2 |
| (9) | 3,5-di-tert-butylbenzene | 3,5-di(trifluoro-methyl)phenyl | 3 | Al | 1 | 2 |
| (10) | Naphthalene | Phenyl | 2 | Zn | 2 | 3 |
| (11) | Naphthalene | Phenyl | 2 | Ca | 2 | 3 |
| (12) | Anthracene | Phenyl | 2 | Ba | 2 | 3 |
| (13) | Anthracene | p-Chlorophenyl | 2 | Zn | 2 | 3 |
| (14) | Phenanthrene | p-Chlorophenyl | 2 | Ba | 2 | 3 |
| (15) | Carbazole | p-Nitrophenyl | 2 | Ca | 2 | 3 |
| (16) | Naphthalene | 3,5-di(trifluoro-methyl)phenyl | 2 | Zn | 2 | 3 |
| (17) | Naphthalene | 3,5-di(trifluoro-methyl)phenyl | 2 | Ba | 2 | 3 |
| (18) | Naphthalene | 1-Naphthyl | 2 | Ca | 2 | 3 |
| (19) | 3,5-di-tert-butylbenzene | 3-trifluoro-methylphenyl | 2 | Zn | 1 | 2 |
| (20) | 3,5-di-tert-butylbenzene | 3-trifluoro-methylphenyl | 2 | Ca | 1 | 2 |
| (21) | 3,5-di-tert-butylbenzene | 4-trifluoro-methylphenyl | 2 | Zn | 1 | 2 |
| (22) | 3,5-di-tert-butylbenzene | p-Chlorophenyl | 2 | Zn | 1 | 2 |
| (23) | 3,5-di-tert-butylbenzene | p-Chlorophenyl | 2 | Ca | 1 | 2 |
| (24) | Naphthalene | 3,5-di(trifluoro-methyl)phenyl | 2 | Ca | 2 | 3 |
| (25) | Naphthalene | 3,5-di(trifluoro-methyl)phenyl | 3 | Al | 2 | 3 |

TABLE 2

| No. | $A^1$ (*1, *2) $A^2$ (*1, *2) | $R^1$ $R^2$ | n | Valency of metal ($m^1$) | Metal ($M^1$) |
|---|---|---|---|---|---|
| (26) | Naphthalene<br>Naphthalene | 3,5-di(trifluoromethyl)phenyl<br>3,5-di(trifluoromethyl)phenyl | 1 | 2 | Zn |
| (27) | Naphthalene<br>Naphthalene | 3,5-di(trifluoromethyl)phenyl<br>3,5-di(trifluoromethyl)phenyl | 1 | 2 | Ca |
| (28) | Naphthalene<br>Naphthalene | 3,5-di(trifluoromethyl)phenyl<br>3,5-di(trifluoromethyl)phenyl | 1 | 2 | Ba |
| (29) | Naphthalene<br>Naphthalene | p-Chlorophenyl<br>p-Chlorophenyl | 1 | 2 | Zn |
| (30) | Naphthalene<br>Naphthalene | p-Chlorophenyl<br>p-Chlorophenyl | 1 | 2 | Ca |
| (31) | Naphthalene<br>Naphthalene | Phenyl<br>Phenyl | 1 | 2 | Ca |
| (32) | Naphthalene<br>Naphthalene | Phenyl<br>Phenyl | 1 | 2 | Zn |
| (33) | Naphthalene<br>Naphthalene | Phenyl<br>Phenyl | 1 | 2 | Ba |
| (34) | Naphthalene<br>Naphthalene | Phenyl<br>Phenyl | 2 | 2 | Zn |
| (35) | Naphthalene<br>Naphthalene | 1-Naphthyl<br>1-Naphthyl | 1 | 2 | Zn |

TABLE 2-continued

| No. | A$^1$ (*1, *2)<br>A$^2$ (*1, *2) | R$^1$<br>R$^2$ | n | Valency of metal (m$^1$) | Metal (M$^1$) |
|---|---|---|---|---|---|
| (36) | Anthracene<br>Anthracene | p-Chlorophenyl<br>p-Chlorophenyl | 1 | 2 | Ca |
| (37) | Naphthalene<br>Benzene | 1-Naphthyl<br>Phenyl | 1 | 2 | Zn |
| (38) | Naphthalene<br>Benzene | 1-Naphthyl<br>Phenyl | 1 | 3 | Al |
| (39) | Naphthalene<br>Naphthalene | p-Chlorophenyl<br>p-Chlorophenyl | 1 | 1 | Na |
| (40) | Naphthalene<br>Naphthalene | p-Chlorophenyl<br>p-Chlorophenyl | 1 | 1 | K |
| (41) | Naphthalene<br>Naphthalene | p-Chlorophenyl<br>p-Chlorophenyl | 1 | 2 | Mg |
| (42) | Naphthalene<br>Naphthalene | p-Chlorophenyl<br>p-Chlorophenyl | 1 | 3 | Al |
| (43) | Naphthalene<br>Naphthalene | p-Chlorophenyl<br>p-Chlorophenyl | 1 | 4 | B |
| (44) | Naphthalene<br>Naphthalene | 3,5-di(trifluoromethyl)phenyl<br>3,5-di(trifluoromethyl)phenyl | 1 | 1 | Na |
| (45) | Naphthalene<br>Naphthalene | 3,5-di(trifluoromethyl)phenyl<br>3,5-di(trifluoromethyl)phenyl | 1 | 1 | K |
| (46) | Naphthalene<br>Naphthalene | 3,5-di(trifluoromethyl)phenyl<br>3,5-di(trifluoromethyl)phenyl | 1 | 2 | Mg |
| (47) | Naphthalene<br>Naphthalene | 3,5-di(trifluoromethyl)phenyl<br>3,5-di(trifluoromethyl)phenyl | 1 | 3 | Al |
| (48) | Naphthalene<br>Naphthalene | 3,5-di(trifluoromethyl)phenyl<br>3,5-di(trifluoromethyl)phenyl | 1 | 4 | B |
| (49) | Naphthalene<br>Naphthalene | Phenyl<br>Phenyl | 1 | 1 | Na |
| (50) | Naphthalene<br>Naphthalene | Phenyl<br>Phenyl | 1 | 2 | Mg |
| (51) | Naphthalene<br>Naphthalene | Phenyl<br>Phenyl | 1 | 3 | Al |
| (52) | Naphthalene<br>Naphthalene | Phenyl<br>Phenyl | 1 | 4 | B |
| (53) | Naphthalene<br>Naphthalene | 1-Naphthyl<br>1-Naphthyl | 1 | 2 | Ca |
| (54) | Naphthalene<br>Naphthalene | 1-Naphthyl<br>1-Naphthyl | 1 | 2 | Mg |
| (55) | Naphthalene<br>Naphthalene | 1-Naphthyl<br>1-Naphthyl | 1 | 3 | Al |
| (56) | Naphthalene<br>Naphthalene | 1-Naphthyl<br>1-Naphthyl | 1 | 4 | B |
| (57) | Anthracene<br>Anthracene | p-Chlorophenyl<br>p-Chlorophenyl | 1 | 2 | Zn |

(*1: With respect to the aromatic ring residue, for example, a benzene ring residue is represented simply by "benzene".
*2: The positions of —(CH$_2$)n-, —O and —CONH—R$^1$ on A$^1$ are 1-, 2- and 3-positions, respectively. The same applies with respect to A$^2$.)

To use the charge controlling agent of the present invention as a toner, at least a resin and a colorant are incorporated to the toner.

The resin for the toner of the present invention may be selected from a wide range including known resins. For example, a styrene resin (a homopolymer or a copolymer of styrene or a substituted styrene) such as a polystyrene, a polychlorostyrene, a poly-α-methyl styrene, a styrene-chlorostyrene copolymer, a styrene-propylene copolymer, a styrene-butadiene copolymer, a styrene-vinyl chloride copolymer, a styrene-vinyl acetate copolymer, a styrene-maleic acid copolymer, a styrene-acrylate copolymer (such as a styrene-methyl acrylate copolymer, a styrene-ethyl acrylate copolymer, a styrene-butyl acrylate copolymer, a styrene-octyl acrylate copolymer or a styrene-phenyl acrylate copolymer), a styrene-methacrylate copolymer (such as a styrene-methyl methacrylate copolymer, a styrene-ethyl methacrylate copolymer, a styrene-butyl methacrylate copolymer or a styrene-phenyl methacrylate copolymer), a styrene-methyl α-chloroacrylate copolymer, or a styrene-acrylonitrileacrylate copolymer, a vinyl chloride resin, a rosin-modified maleic acid resin, a phenol resin, an epoxy resin, a saturated or unsaturated polyester resin, a low molecular weight polyethylene, a low molecular weight polypropylene, an ionomer resin, a polyurethane resin, a silicone resin, a ketone resin, an ethylene-ethyl acrylate copolymer, a xylene resin, or a polyvinyl butyral resin, may be mentioned. Particularly preferred as the resin to be used in the present invention, is a styrene-acrylate copolymer, a styrene-methacrylate copolymer, a saturated or unsaturated polyester resin or an epoxy resin. These resins may be used alone or in combination as a mixture of two or more of them.

The colorant to be incorporated to the toner of the present invention may be selected from a wide range including known colorants. For example, carbon black, lamp black, iron black, ultramarine blue, Nigrosine dye, aniline blue, phthalocyanine blue, phthalocyanine green, Hansa Yellow, Chrome Yellow, Rose Bengale, a triarylmethane type dye, a monoazo dye pigment, or a disazo dye pigment may be mentioned.

The metallic compound of a compound of the above formula (I) or (II) is pale yellow and may be incorporated to a colored toner of e.g. blue, red or yellow, which may be used for full color development. In such a case, a colorant composed of a dye pigment having the corresponding color, is used. The content of the colorant is preferably from 3 to 20 parts by weight, per 100 parts by weight of the resin.

As a method for incorporating the metallic compound of a compound of the above formula (I) or (II) and other charge controlling agent to the toner of the present invention, it is possible to employ an internally incorporating method wherein they are added and mixed together with a resin into the toner, or an externally incorporating method wherein they are added after forming toner particles. The internally incorporating method is more common and preferred.

The content of the metallic compound of a compound of the formula (I) or (II) in the toner is preferably from 0.1 to 20 parts by weight, more preferably from 0.1 to 15 parts by weight, still more preferably from 0.5 to 5 parts by weight, per 100 parts by weight of the resin. If the content of the metallic compound of a compound of the formula (I) or (II) is too small, the effect of improving the electric charge property of a toner can not be improved, and if it is excessive, the quality of the toner tends to deteriorate.

To the toner of the present invention, in addition to the metallic compound of a compound of the above formula (I) or (II), other charge controlling agents inclusive of known agents, such as a Nigrosine dye, a quaternary ammonium salt or a metal-containing complex compound, may be incorporated. Further, to the toner of the present invention, other known additives such as a solid electrolyte, a polymer electrolyte, a charge transfer complex, an electroconductor of e.g. a metal oxide such as tin oxide, a semiconductor or a ferroelectric substance, a magnetic substance, etc., may be incorporated to control the electrical properties of the toner. Further, for the purpose of controlling the thermal properties or physical properties, additives of e.g. various plasticizers or release agents such as a low molecular weight olefin polymer may also be incorporated to the toner. Further, it is possible to add fine powder of $TiO_2$, $Al_2O_3$ or $SiO_2$ to the toner and to cover the surface of toner particles with it to improve the flowability or aggregation resistance of the toner.

The charge controlling agent of the present invention is particularly useful for a negatively chargeable toner.

The toner may be prepared by a method which comprises kneading the above-mentioned various components by e.g. a kneader, followed by cooling and then by pulverization and classification. However, the toner may be a capsulated toner or a polymerized toner. The toner of the present invention may be applied not only to a dual-component developer but also to a so-called mono-component developer (a magnetic toner or a non-magnetic toner) such as a magnetite-containing toner. The average particle size of the toner is preferably from 5 to 20 μm.

As the carrier to be mixed with the toner of the present invention to form a developer, a magnetic material such as a conventional iron powder type, ferrite type or magnetite type carrier, the one having a resin coating applied to the surface of such magnetic material or a magnetic resin carrier, may be employed. As the coating resin for a resin coating carrier, a commonly known styrene type resin, an acryl type resin, a styrene-acryl copolymer type resin, a silicone type resin, a modified silicone type resin, a fluorine type resin or a mixture of such resins may be used, but the coating resin is not limited to such specific examples. The average particle size of the carrier is not particularly limited, but the one having an average particle size of from 10 to 200 μm is preferred. Such a carrier is preferably used in a content of from 5 to 100 parts by weight, per part by weight of the toner.

Now, application of the charge controlling agent of the present invention to a charge-imparting material will be described.

The charge-imparting material has the metallic compound of a compound of the above formula (I) or (II) at least on a part of its surface.

The charge-imparting material of the present invention can be obtained by forming a coating layer containing the charge controlling agent of the present invention on a base material by a method wherein a coating liquid obtained by dissolving or dispersing the charge controlling agent of the present invention in a solvent or a dispersing medium, if necessary, together with a binder resin, is coated on the base material for the charge-imparting material by dipping, spraying or brush coating, or in the case where the base material is carrier particles, by a method wherein such carrier particles are impregnated and mixed with the above coating liquid, followed by drying, or a method wherein coating is carried out by a fluidized bed of a direct mixture with the base material. Otherwise, a charge-imparting material may be prepared by directly melt-kneading a binder resin and the charge controlling agent, and extruding and laminating the kneaded material on a base material. Further, the charge controlling agent may be incorporated into a moldable resin, and the mixture is molded in the form of carrier particles, a developing sleeve or a layer-forming blade to obtain a charge-imparting material.

The charge controlling agent for electrostatic image development of the present invention is excellent in safety and has a sufficient charge level and charge stability, and it is a charge controlling agent for electrostatic image-development of high quality, whereby no copy staining will result even by continuous copying.

Now, the present invention will be described in further detail with reference to Examples. In the following Examples, "parts" means "parts by weight".

EXAMPLE 1

| | |
|---|---|
| Polyester resin (FC-023, manufactured by Mitsubishi Rayon Co., Ltd.) | 100 parts |
| Carbon black (#44, manufactured by Mitsubishi Chemical Corporation) | 4 parts |
| Compound No. (1) | 3 parts |

The above materials were blended and kneaded, followed by pulverization and classification to obtain a black toner having an average particle size of 11 μm. Five parts of this toner and 100 parts of an acryl resin-coated carrier having an average particle size of about 100 μm, were mixed and stirred to obtain a developer. Then, using this developer, a copy was taken by a copying machine employing selenium as a photoreceptor, whereby a clear copy was obtained.

EXAMPLE 2

The operation was conducted in the same manner as in Example 1 except that 1 part of compound (5) was used as the charge controlling agent, whereby a clear copy was obtained as in Example 1.

EXAMPLE 3

The operation was conducted in the same manner as in Example 1 except that 1 part of compound (6) was used as the charge controlling agent, whereby a clear copy was obtained as in Example 1.

EXAMPLE 4

The operation was conducted in the same manner as in Example 1 except that 3 parts of compound (8) was used as the charge controlling agent, whereby a clear copy was obtained as in Example 1.

EXAMPLE 5

The operation was conducted in the same manner as in Example 1 except that 1 part of compound (10) was used as the charge controlling agent, whereby a clear copy was obtained as in Example 1.

EXAMPLE 6

The operation was conducted in the same manner as in Example 1 except that 3 parts of compound (11) was used as the charge controlling agent, whereby a clear copy was obtained as in Example 1.

EXAMPLE 7

The operation was conducted in the same manner as in Example 1 except that 3 parts of compound (21) was used as the charge controlling agent, whereby a clear copy was obtained as in Example 1.

EXAMPLE 8

The operation was conducted in the same manner as in Example 1 except that 3 parts of compound (22) was used as the charge controlling agent, whereby a clear copy was obtained as in Example 1.

EXAMPLE 9

The operation was conducted in the same manner as in Example 1 except that 3 parts of compound (26) was used as the charge controlling agent, whereby a clear copy was obtained as in Example 1.

EXAMPLE 10

The operation was conducted in the same manner as in Example 1 except that 3 parts of compound (27) was used as the charge controlling agent, whereby a clear copy was obtained as in Example 1.

EXAMPLE 11

The operation was conducted in the same manner as in Example 1 except that 1 part of compound (29) was used as the charge controlling agent, whereby a clear copy was obtained as in Example 1.

EXAMPLE 12

The operation was conducted in the same manner as an Example 1 except that 1 part of compound (30) was used as the charge controlling agent, whereby a clear copy was obtained as in Example 1.

EXAMPLE 13

The operation was conducted in the same manner as in Example 1 except that 3 parts of compound (32) was used as the charge controlling agent, whereby a clear copy was obtained as in Example 1.

EXAMPLE 14

The operation was conducted in the same manner as an Example 1 except that 3 parts of compound (34) was used as the charge controlling agent, whereby a clear copy was obtained as in Example 1.

EXAMPLE 15

The operation was conducted in the same manner as in Example 1 except that 3 parts of compound (35) was used as the charge controlling agent, whereby a clear copy was obtained as in Example 1.

EXAMPLE 16

The operation was conducted in the same manner as in Example 1 except that 3 parts of compound (37) was used as the charge controlling agent, whereby a clear copy was obtained as in Example 1.

EXAMPLE 17

The operation was conducted in the same manner as in Example 1 except that 3 parts of compound (39) was used as the charge controlling agent, whereby a clear copy was obtained as in Example 1.

EXAMPLE 18

The operation was conducted in the same manner as in Example 1 except that 1 part of compound (42) was used as the charge controlling agent, whereby a clear copy was obtained as in Example 1.

EXAMPLE 19

The operation was conducted in the same manner as in Example 1 except that 1 part of compound (43) was used as the charge controlling agent, whereby a clear copy was obtained as in Example 1.

EXAMPLE 20

The operation was conducted in the same manner as in Example 1 except that 3 parts of compound (46) was used as the charge controlling agent, whereby a clear copy was obtained as in Example 1.

EXAMPLE 21

The operation was conducted in the same manner as in Example 1 except that 3 parts of compound (47) was used as the charge controlling agent, whereby a clear copy was obtained as in Example 1.

EXAMPLE 22

The operation was conducted in the same manner as in Example 1 except that 3 parts of compound (53) was used as the charge controlling agent, whereby a clear copy was obtained as in Example 1.

EXAMPLE 23

The operation was conducted in the same manner as in Example 1 except that 3 parts of compound (54) was used as the charge controlling agent, whereby a clear copy was obtained as in Example 1.

EXAMPLE 24

The operation was conducted in the same manner as in Example 1 except that 3 parts of compound (55) was used as the charge controlling agent, whereby a clear copy was obtained as in Example 1.

EXAMPLE 25

The operation was conducted in the same manner as in Example 1 except that 1 part of compound (57) was used as the charge controlling agent, whereby a clear copy was obtained as in Example 1.

EXAMPLE 26 AND COMPARATIVE EXAMPLES 1 AND 2

| | |
|---|---|
| Polyester resin | 100 parts |
| Carbon black | 4 parts |
| Charge controlling agent in Table 3 | 3 parts |

The above materials were blended and kneaded, followed by pulverization and classification to obtain a black toner. Then, 0.5 g of the black toner and 9.5 g of a carrier composed of ferrite powder were put into a glass bottle and shaked for 5 minutes, whereupon the quantity of the electric charge was measured by a blow off method.

TABLE 3

| | Charge controlling agent | Quantity of electric charge μC/g |
|---|---|---|
| Example 26 | Compound (29) | −35.5 |
| Comparative Example 1 | —OH form of Compound (29) | −29.5 |
| Comparative Example 2 | Chromium-containing metal monoazo dye * | −28.0 |

* Tradename S-34, manufactured by Orient Chemical Industries, Ltd.

From this experiment, it is apparent that the compound of the present invention has an increased quantity of electric charge in a metal-containing form, and it has a superior charge-imparting property than a conventional charge controlling agent of metal-containing type.

EXAMPLES 27 TO 31 AND COMPARATIVE EXAMPLES 3 AND 4

| | |
|---|---|
| Polyester resin | 100 parts |
| Carbon black | 4 parts |
| Charge controlling agent in Table 4 | 3 parts |

The above materials were blended and kneaded, followed by pulverization and classification to obtain a black toner. Then, 10 g of the black toner and 30 mg of fine SiO$_2$ powder were mixed. The mixture was put into a developing tank of non-magnetic mono-component developing system comprising a rubber roller and a blade made of urethane, and the roller was rotated a predetermined number of time, whereupon the quantity of the electric charge of the toner on the roller was measured by a suction method.

TABLE 4

| | Charge controlling agent | Quantity of electric charge μC/g |
|---|---|---|
| Example 27 | Compound (26) | −10 |
| Example 28 | Compound (27) | −9.1 |
| Example 29 | Compound (29) | −10 |
| Example 30 | Compound (35) | −9.5 |
| Example 31 | Compound (41) | −10 |

TABLE 4-continued

| | Charge controlling agent | Quantity of electric charge μC/g |
|---|---|---|
| Comparative Example 3 | —OH form of Compound (29) | −7.4 |
| Comparative Example 4 | —OH form of Compound (35) | 0 |

From this experiment, it is apparent that the compound of the present invention has an increased quantity of electric charge in a metal-containing form.

We claim:

1. A charge controlling agent for electrostatic image development, which is a metallic compound of a compound of the formula (I):

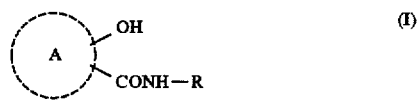

wherein each of A and R is a substituted or unsubstituted aromatic ring residue, and —O and —CONH—R are bonded to positions adjacent to each other on the aromatic ring residue A, or the formula (II):

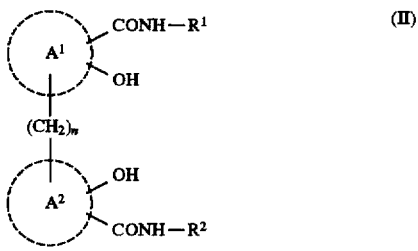

wherein each of A$^1$, A$^2$, R$^1$ and R$^2$ is a substituted or unsubstituted aromatic ring residue, n is an integer, and —O and —CONHR$^1$, and —O and —CONH—R$^2$, are bonded to positions adjacent to each other on the aromatic ring residues A$^1$ and A$^2$, respectively.

2. The charge controlling agent for electrostatic image development according to claim 1, wherein A, R, A$^1$, A$^2$, R$^1$ or R$^2$ is a substituted or unsubstituted benzene ring residue, a substituted or unsubstituted naphthalene ring residue, a substituted or unsubstituted anthracene ring residue, a substituted or unsubstituted phenanthrene ring residue, a substituted or unsubstituted carbazole ring residue, a substituted or unsubstituted fluorene ring residue, a substituted or unsubstituted fluorenone ring residue, a substituted or unsubstituted dibenzofuran ring residue, a substituted or unsubstituted dibenzothiophene ring residue, or a substituted or unsubstituted benzocarbazole ring residue.

3. The charge controlling agent for electrostatic image development according to claim 2, wherein A, R, A$^1$, A$^2$, R$^1$ or R$^2$ is a substituted or unsubstituted benzene ring residue, or a substituted or unsubstituted naphthalene ring residue.

4. The charge controlling agent for electrostatic image development according to claim 1, wherein the substituent of A, R, A$^1$, A$^2$, R$^1$ or R$^2$, is a C$_{1-5}$ alkyl group, a haloalkyl group, an amino group, an alkoxyl group, a halogen atom, a nitro group or a phenyl group.

5. The charge controlling agent for electrostatic image development according to claim 4, wherein the substituent of A, R, A$^1$, A$^2$, R$^1$ or R$^2$ is a C$_{1-5}$ alkyl group, a haloalkyl group or a halogen atom.

6. The charge controlling agent for electrostatic image development according to claim 1, wherein n is an integer of from 1 to 5.

7. The charge controlling agent for electrostatic image development according to claim 1, wherein the metal of the metallic compound of a compound of the formula (I) is a bivalent to tetravalent metal.

8. The charge controlling agent for electrostatic image development according to claim 1, wherein the metal of the metallic compound of a compound of the formula (II) is a monovalent to tetravalent metal.

9. The charge controlling agent for electrostatic image development according to claim 7, wherein the metal of the metallic compound of a compound of the formula (I) is Zn, Ca, Mg or Al.

10. The charge controlling agent for electrostatic image development according to claim 8, wherein the metal of the metallic compound of a compound of the formula (II) is Zn, Ca, Mg or Al.

11. An electrostatic image-developing toner comprising a resin, a colorant and a charge controlling agent for electrostatic image development as defined in claim 1.

12. The electrostatic image-developing toner according to claim 11, wherein the content of the charge controlling agent for electrostatic image development is from 0.1 to 20 parts by weight, per 100 parts by weight of the resin.

13. A charge-imparting material for electrostatic image development having a charge controlling agent for electrostatic image development as defined in claim 1 at least on a part of the surface of its base material.

* * * * *